United States Patent
Damiani et al.

(10) Patent No.: US 10,264,787 B1
(45) Date of Patent: Apr. 23, 2019

(54) NATURAL MOSQUITO LARVICIDE

(71) Applicant: BIOVECBLOK, s.r.l., Camerino (IT)

(72) Inventors: Claudia Damiani, Petriolo (IT); Aurelio Serrao, Crotone (IT); Matteo Valzano, Pioraco (IT); Vincenzo Cuteri, Castelraimondo (IT); Riccardo Arigoni, Lecco (IT)

(73) Assignee: BIOVECBLOK s.r.l., Camerino (IT)

( * ) Notice: Subject to any disclaimer, the term of this patent is extended or adjusted under 35 U.S.C. 154(b) by 0 days.

(21) Appl. No.: 15/926,434

(22) Filed: Mar. 20, 2018

Related U.S. Application Data

(60) Provisional application No. 62/591,325, filed on Nov. 28, 2017.

(51) Int. Cl.
| | | |
|---|---|---|
| A01N 25/02 | (2006.01) | |
| A01N 37/44 | (2006.01) | |
| A01N 31/02 | (2006.01) | |
| A01N 25/04 | (2006.01) | |
| A01N 65/00 | (2009.01) | |
| A01N 37/40 | (2006.01) | |

(52) U.S. Cl.
CPC .............. *A01N 37/44* (2013.01); *A01N 25/04* (2013.01); *A01N 31/02* (2013.01); *A01N 37/40* (2013.01); *A01N 65/00* (2013.01)

(58) Field of Classification Search
CPC ...... A01N 25/006; A01N 25/02; A01N 33/02; A01N 37/44; A01N 31/02; A01N 37/40; A01N 25/04
See application file for complete search history.

(56) References Cited

U.S. PATENT DOCUMENTS

| | | | |
|---|---|---|---|
| 4,929,608 A | 5/1990 | Mahmood | |
| 5,196,200 A | 3/1993 | Wilson et al. | |
| 5,205,065 A | 4/1993 | Wilson et al. | |
| 5,228,233 A | 7/1993 | Butler et al. | |
| 5,281,621 A | 1/1994 | Wilson et al. | |
| 5,327,675 A | 7/1994 | Butler et al. | |
| 5,417,009 A | 5/1995 | Butler et al. | |
| 5,464,626 A | 11/1995 | Warren et al. | |
| 5,521,165 A | 5/1996 | Warren et al. | |
| 5,633,236 A | 5/1997 | Warren et al. | |
| 5,665,781 A | 5/1997 | Warren et al. | |
| 5,698,210 A | 12/1997 | Levy | |
| 5,716,602 A | 2/1998 | Uick | |
| 5,855,903 A | 1/1999 | Warren et al. | |
| 5,965,137 A | 10/1999 | Petrus | |
| 6,077,521 A | 6/2000 | Hammond et al. | |
| 6,267,953 B1 | 7/2001 | Bernier et al. | |
| 6,306,415 B1 | 10/2001 | Reifenrath | |
| 6,538,027 B2 | 3/2003 | Manker et al. | |
| 6,548,085 B1 | 4/2003 | Zobitne et al. | |
| 6,555,121 B1 | 4/2003 | Bessette et al. | |
| 6,562,841 B1 | 5/2003 | Klun et al. | |
| 6,593,299 B1 | 7/2003 | Bennett et al. | |
| 6,605,643 B1 | 8/2003 | Ross | |
| 6,719,959 B1 | 4/2004 | Gonzalez et al. | |
| 6,800,294 B1 | 10/2004 | Ryan et al. | |
| 6,809,078 B2 | 10/2004 | Baum et al. | |
| 6,825,006 B2 | 11/2004 | Baum et al. | |
| 7,144,591 B2 | 12/2006 | Bencsits | |
| 7,198,797 B2 | 4/2007 | O'Brien | |
| 7,201,926 B2 | 4/2007 | Fried et al. | |
| 7,232,844 B2 | 6/2007 | Hallahan | |
| 7,344,728 B1 | 3/2008 | Perry | |
| 7,378,557 B1 | 5/2008 | Zhang et al. | |
| 7,381,431 B2 | 6/2008 | Baker et al. | |
| 7,531,188 B2 | 5/2009 | Jones, Jr. | |
| 7,858,127 B2 | 12/2010 | Overman | |
| 7,985,432 B2 | 7/2011 | Baker et al. | |
| 8,454,983 B2 | 6/2013 | DeChant et al. | |
| 8,568,800 B2 | 10/2013 | Tumbers | |
| 8,647,684 B2 | 2/2014 | Baube | |
| 8,663,615 B2 | 3/2014 | Albee, Jr. et al. | |
| 8,696,987 B2 | 4/2014 | Solomon et al. | |
| 8,742,204 B2 | 6/2014 | Turano et al. | |
| 8,900,553 B2 | 12/2014 | Tamarkin et al. | |
| 8,999,407 B2 | 4/2015 | Salomon et al. | |
| 9,079,152 B2 | 7/2015 | Markus et al. | |
| 9,101,143 B2 | 8/2015 | Markus et al. | |
| 9,210,926 B2 | 12/2015 | Markus et al. | |
| 9,326,524 B1 | 5/2016 | Jack et al. | |
| 9,433,203 B2 | 9/2016 | Lancaster, Jr. | |
| 9,549,898 B2 | 1/2017 | Tamarkin et al. | |
| 9,717,240 B2 | 8/2017 | Markus et al. | |
| 2007/0154504 A1 | 4/2007 | Coats et al. | |
| 2008/0193387 A1 | 8/2008 | De Wolff | |
| 2008/0213198 A1 | 9/2008 | Lintner et al. | |
| 2009/0018192 A1 | 1/2009 | Zhang et al. | |
| 2010/0233146 A1 | 9/2010 | McDaniel | |
| 2010/0310685 A1* | 12/2010 | Principato | A01N 31/02 424/747 |
| 2011/0212146 A1* | 9/2011 | Helland | A61K 8/06 424/401 |

(Continued)

FOREIGN PATENT DOCUMENTS

WO 2016018937 2/2016

OTHER PUBLICATIONS

Quevedo et al. (Res Chem Intermed 2015:31;5283-5292). (Year: 2015).*

(Continued)

*Primary Examiner* — Ernst V Arnold
(74) *Attorney, Agent, or Firm* — The Roy Gross Law Firm, LLC; Roy Gross

(57) ABSTRACT

Larvicide and pupicide formulation and methods of administration thereof, harmless for humans and other animals, able to kill all the instars larval stages and pupae in about two hours and fifteen minutes, respectively, with no impact on the environment. Larvicide/pupicide formulation and methods of administration thereof for killing larvae and pupae of *Anopheles gambiae* and *An. stephensi*, main vectors of malaria, and *Aedes aegypti* and *Ae. albopictus*, main vectors of dengue, Zika virus, chikungunya and yellow fever.

18 Claims, 1 Drawing Sheet

(56) References Cited

U.S. PATENT DOCUMENTS

2011/0229543 A1    9/2011  DeChant et al.
2013/0296370 A1   11/2013  Di Martino et al.
2016/0360758 A1* 12/2016  Dale .................... A01N 63/04
2017/0215432 A1    8/2017  Nair

OTHER PUBLICATIONS

Costa et al. (Abstract of: J Med Entomol May 2017: 54(3);670-676); 2 pages. (Year: 2017).*
Ansari et al. (Bioresource Technology 2000;71:267-271). (Year: 2000).*

* cited by examiner

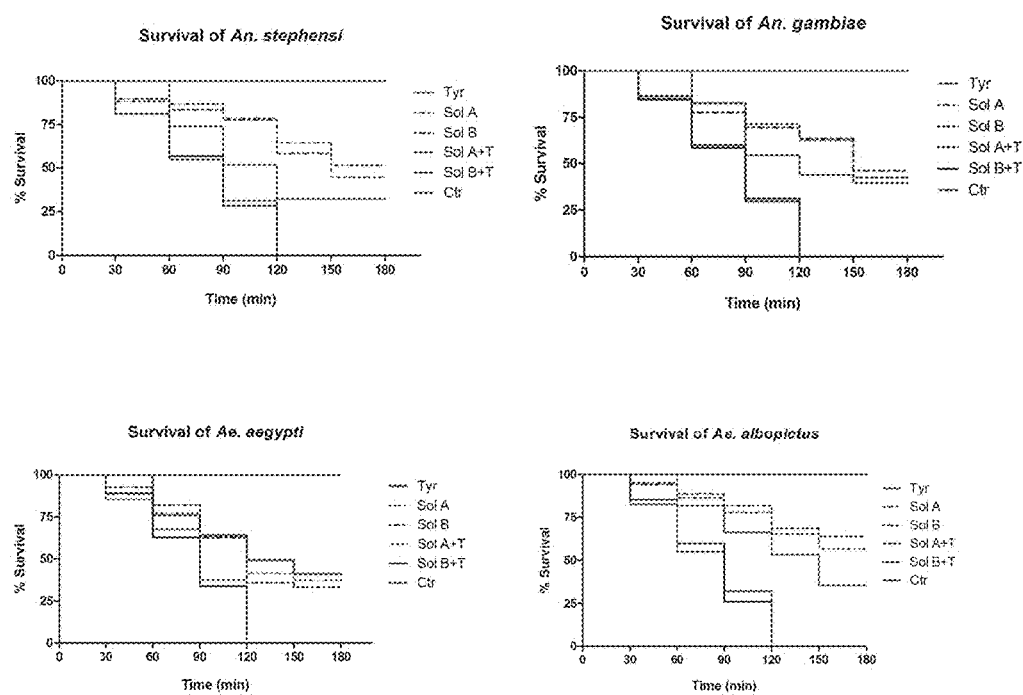
Fig. 1: Survival tests of the four mosquito species *An. stephensi*, *An. gambiae*, *Ae. aegypti* and *Ae. albopictus* treated with different formulations.

NATURAL MOSQUITO LARVICIDE

CROSS REFERENCE TO RELATED APPLICATIONS

This application claims the benefit of priority of U.S. Provisional Patent Application No. 62/591,325 filed Nov. 28, 2017 entitled NATURAL MOSQUITO LARVICIDE. The contents of this application are incorporated by referenced as if fully set forth herein.

OF THE INVENTION

The present invention is directed to larvicide formulation and methods of administration thereof for killing the instars larval stages and pupae in about two hours and fifteen minutes, respectively; with no impact on the environment. In particular, the larvicide formulation and methods of administration thereof are directed to killing larvae and pupae of *Anopheles gambiae* and *An. stephensi*, main vectors of malaria, and *Aedes aegypti* and *Ae. albopictus*, main vectors of dengue, Zika virus, chikungunya and yellow fever. In particular, the present invention relates to a pupicidal and larvicidal composition suitable to be placed in environments frequented by human beings and by confined or nonconfined domestic and nondomestic animals and particularly suitable for eliminating the juvenile stages of mosquitoes.

BACKGROUND

Mosquitoes represent a wide number of insects belonging to the order Diptera, suborder Nematocera, family Culicidae. There are approximately 3500 species of mosquitoes grouped into 41 genera.

Vector-borne diseases transmitted by mosquitoes (malaria, filariasis, dengue, chikungunya, yellow fever, Zika virus and other arboviruses) are the major public health concerns in tropical and sub-tropical areas of the world. Poor and ineffective drainage systems in urban areas, especially during rainy seasons, and irrigation ditches in farmland provide several mosquito breeding places.

Among the mosquito populations, *Anopheles stephensi* and *An. gambiae* are the main malaria vectors in Asia and Africa, respectively; whereas *Aedes aegypti* and *Ae. albopictus* are the main vectors of arboviruses.

All these vector-borne diseases afflict mainly poor countries where more than two billion people live in endemic regions.

The common approaches to fight vector-borne diseases rely on the use of chemical insecticides or synthetic larvicides targeting adults and larvae. However, the development of mosquitoes showing insecticide-resistance to different classes of synthetic compounds, such as pyrethroids, organophosphates, organochlorides and carbamates, has determined the research of new and "safe" formulations to control mosquito populations. Moreover, the toxicity of available chemical products on human beings and animals as well, their high operational costs and the subsequent environmental pollution, have caused the need for developing new approaches to control vector-borne diseases.

Mosquito Life Cycle

Mosquitoes go through four developmental stages in their life cycles: eggs, larvae, pupae and adult. The first three stages are aquatic and persist until about two weeks and depend on the mosquito species and the external environmental conditions. The female mosquito lifespan is around three weeks while for a male it's just two weeks. Adult females lay 50-200 eggs per oviposition. The eggs are quite small (about 0.5×0.2 mm). Eggs are laid singly and directly on water. Eggs are not resistant to drying and hatch within 2-3 days, although hatching may take up to 2-3 weeks in colder climates.

Larvae emerge from the eggs. The *Anopheles* larvae do not present a respiratory siphon, like other mosquitoes (e.g. the *Culex* and *Aedes* genera), so its body is parallel to the surface of the water. In contrast, feeding larvae of non-anopheline mosquito species attach itself to the water surface through its posterior siphon, with their body pointing downwards. The mosquito larvae have a well-developed head with mouth brushes used for feeding, a large thorax and a nine-segment abdomen. The larvae feed on zooplankton, algae, bacteria, and other microorganisms in the surface microlayer.

To lay their eggs female mosquitoes need to mate, to inseminate the eggs and one or more blood feeding to develop the eggs. Immediately after the oviposition, freshly oviposited eggs are soft and white. Since the eggshell in insects represents an important barrier that prevent the embryo from damages and infections, for this reason it undergoes through different processes of hardening and darkening that gives to it more resistance to external environment. In this sense, the amino acid tyrosine plays a crucial role in the egg chorion melanization. In the melanization pathway, tyrosine is converted in L-Dopa by tyrosine hydroxylase and L-Dopa is converted in dopamine by Dopa decarboxylase, different prophenol oxidase are then involved in the formation in both L-Dopa melanin from L-Dopa and Dopamine melanin from Dopamine.

Larvae develop through four stages, or instars, after which they develop into pupae. At the end of each instars, the larvae grow up, modifying their exoskeletons, to allow for further growth. First-stage larvae are about 1 mm in length; fourth-stage larvae are normally 5-8 mm in length.

The processes from egg-laying to adult inception depends on temperature and environmental conditions, with a minimum time of seven days.

The larvae can survive in a wide range of habitats and they have been found in freshwater or saltwater marshes, swamps, rice fields, the edges of streams and rivers, and small, temporary rain pools.

The pupae have the shape of a comma if it's seen from the side. The head and thorax are joined into a cephalothorax with the abdomen curving around underneath. As with the larvae, pupae must come to the surface frequently to breathe, through a pair of respiratory trumpets on their cephalothoraces. After a few days as a pupa, the dorsal surface of the cephalothorax is broken and the adult mosquito emerges. The pupal stage lasts around 2-3 days in temperate areas.

The duration from egg to adult can considerably vary depending on species, and it is strongly influenced by external environment. Mosquitoes can develop from egg to adult from 7 to 14 days according to environmental conditions.

Most existing insecticides available in the market are constituted by effective ingredients but are also characterized by specific toxicity degrees for human beings and animals, as well.

The elimination of mosquito larvae and pupae using a not-toxic formulation does not pollute aquatic environments substantially eliminating risk of intoxication for both animals and human beings.

Existing references known to kill mosquitoes include U.S. Pat. Nos. 5,196,200, 5,205,065, 5,228,233, 5,281,621, 5,327,675, 5,417,009, 5,464,626, 5,521,165, 5,633,236, 5,665,781, 5,698,210, 5,716,602, 5,855,903, 6,077,521, 6,267,953, 6,306,415, 6,562,841, 6,593,299, 6,605,643, 6,800,294, 6,809,078, 6,825,006, 7,198,797, 7,378,557, 8,454,983, 8,696,987, 8,900,553, 9,549,898, US20070154504, US20080193387, US20080213198, US20090018192, US20100233146, US20100310685, US20110229543, US20130296370, US20160360758, US20170215432 and WO2016018937.

It is an object of the invention to improve upon the deficiencies in the prior art.

SUMMARY OF THE INVENTION

It is an object of the invention to improve upon the prior art and to provide larvicide formulations and methods of administration thereof for killing the instars larval stages and pupae in about two hours and fifteen minutes, respectively; with no impact on the environment.

It is an object of the invention to provide a larvicide formulation and methods of administration thereof for killing larvae and pupae of *Anopheles gambiae* and *An. stephensi*, main vectors of malaria, and *Aedes aegypti* and *Ae. albopictus*, main vectors of dengue, Zika virus, chikungunya and yellow fever.

It is an object of the invention to provide a larvicidal and pupicidal formulation characterized by a substantially negligible toxicity for animals, particularly fish, and for human beings.

It is an object of the present invention to provide a larvicidal and pupicidal formulation which has a low cost, is relatively simple to employ in practice, and is safe in application.

It is an object of the invention to provide a larvicidal and pupicidal formulation comprising: cetyl alcohol, salicylic acid, tyrosine, peppermint oil, *eucalyptus* oil, diatomaceous earth and tween 20.

Other objects of the invention are achieved by providing methods of administering a larvicide and pupicidal formulation comprising: cetyl alcohol, salicylic acid, tyrosine, peppermint oil, *eucalyptus* oil, diatomaceous earth and tween 20.

In particular, objects of the invention are achieved by providing an emulsion for killing mosquitoes, comprising: tyrosine dissolved in water; and a solution of cetyl alcohol and salicylic acid dissolved in peppermint oil, wherein the emulsion is configured to be applied as a larvicide and pupicide to kill larvae and pupae of mosquitoes.

In certain embodiments, the solution further comprises diatomaceous earth, tween 20 and *eucalyptus* oil dissolved in said peppermint oil.

In certain embodiments, the larvae and pupae are selected from a group consisting of *Anopheles gambiae* and *An. stephensi*, main vectors of malaria, and *Aedes aegypti* and *Ae. albopictus*, main vectors of dengue, Zika virus, chikungunya and yellow fever.

In certain embodiments, the emulsion kills the larvae and pupae within about two hours and fifteen minutes, respectively.

In certain embodiments, the emulsion comprises 0.03 g of said tyrosine, 200 ml of said water, 10 g of said cetyl alcohol, 10 g of said salicylic acid and 100 ml of peppermint oil.

In certain embodiments, the emulsion comprises 0.03 g of said tyrosine, 200 ml of said water, 10 g of said cetyl alcohol, 10 g of said salicylic acid, 5 g of diatomaceous earth and 20 drops of tween 20 dissolved into 40 ml of *eucalyptus* oil and 60 ml of peppermint oil.

In certain embodiments, the ratio of tyrosine to water in the emulsion ranges from 0% to 1%.

In certain embodiments, the ratio of cetyl alcohol to peppermint oil ranges from 0% to 30%.

In certain embodiments, the ratio of salicylic acid to peppermint oil ranges from 0% to 30%.

In certain embodiments, the ratio of diatomaceous earth to peppermint oil ranges from 0% to 20%.

In certain embodiments, the ratio of tween 20 to peppermint oil ranges from 0% to 20%.

In certain embodiments, the ratio of *eucalyptus* oil to peppermint oil ranges from 0% to 70%.

In certain embodiments, the larvae mortality is at least 60% after 24 hours post application of said emulsion.

In certain embodiments, the larvae mortality is at least 70% after 18 hours post application of said emulsion.

In certain embodiments, the larvae and pupae mortality is approximately 100% after 2 hours and 15 minutes, respectively, after application of said emulsion.

Other objects of the invention are achieved by providing an emulsion for killing mosquitoes, comprising: tyrosine dissolved in water; and an oil-based solution comprising peppermint oil, wherein the emulsion is configured to be applied as a larvicide/pupicide to kill larvae and pupae of mosquitoes.

In certain embodiments, the oil-based solution comprises cetyl alcohol and salicylic acid.

In certain embodiments, the oil-based solution comprises diamatoceous earth and tween 20.

Other objects of the invention are achieved by providing a method of administering the larvicide/pupicide emulsion of the embodiments of the invention as larvicide/pupicide to kill larvae and pupae of mosquitoes.

In certain embodiments, the larvae and pupae are selected from a group consisting of *Anopheles gambiae* and *An. stephensi*, main vectors of malaria, and *Aedes aegypti* and *Ae. albopictus*, main vectors of dengue, Zika virus, chikungunya and yellow fever.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 1 shows charts of survival tests of the four mosquito species in particular with *An. stephensi, An. gambiae, Ae. aegypti* and *Ae. albopictus* treated with different formulations.

DETAILED DESCRIPTION OF INVENTION

In the following description, numerous details are set forth for the purpose of explanation. However, one of ordinary skill in the art will realize that the invention may be practiced without the use of these specific details.

The formulations of pupicidal and/or larvicidal compositions according to the invention are intended to suppress larvae and pupae of *Anopheles stephensi* and *An. gambiae*, main vectors of malaria; *Aedes albopictus* and *Ae. aegypti*, vectors of several arboviruses, by means of active ingredients and excipients which have low toxicity.

The composition according to the invention comprises cetyl alcohol.

Cetyl alcohol, also known as 1-hexadecanol and palmityl alcohol, is a solid organic compound and a member of the alcohol class of compounds. Its chemical formula is $CH_3(CH_2)_{15}OH$. At room temperature, cetyl alcohol takes the form of a waxy white solid or flakes. It belongs to the group of fatty alcohols. With the demise of commercial whaling, cetyl alcohol is no longer primarily produced from whale oil, but instead either as an end-product of the petroleum industry, or produced from vegetable oils such as palm oil and coconut oil. From a functional standpoint, it must be specified that specific researches that have been conducted show that cetyl alcohol is an excellent pupicidal compounds of Diptera.

Cetyl alcohol is a long chain alcohol, which can find applications as an emulsifying agent, adjuvant in the stabilization of certain products, emollient, viscosity increasing agent, foam booster and opacifying agent in pharmaceuticals and cosmetics. The composition according to the invention may also comprise essential oils: in particular, the embodiments showing optimum effectiveness in suppressing larvae and pupae of mosquitoes include essential oil of peppermint. Peppermint Oil is an essential oil extracted from the leaves of *Menthaxpiperita*. Peppermint oil is used for its aromatic properties and as a flavoring and to treat illnesses of the digestive and respiratory system as well as pain. Said essential oil guarantees the formation of a film, on the free surface of the water in which the product is distributed (ponds, lakes or natural or artificial bodies of water of any other kind and/or size); this film of infinitesimal thickness assures contact of the larvae and/or pupae with the compound.

The composition may also include tyrosine. Tyrosine is one of the 20 standard amino acids that are used by cells to synthesize proteins. It is a non-essential amino acid with a polar side group. Its codons are UAC and UAU. Tyrosine is actually found in many high-protein food products such as chicken, turkey, fish, milk, yogurt, cottage cheese, cheese, peanuts, almonds, pumpkin seeds, sesame seeds, soy products, lima beans, avocados, and bananas.

The composition may also include tween 20. It is a nonionic detergent widely used in biochemical applications. It has been used as an emulsifying agent for the preparation of stable oil-in-water emulsions.

The embodiments comprise salicylic acid. Salicylic acid is a monohydroxybenzoic acid which shows bacteriostatic, fungicidal and keratolytic actions. It is soluble in water, biodegradable in nature having low bioaccumulation potential. Salicylic acid and its derivatives are also used in pharmaceutical and cosmetic industry. Likewise, salicylic acid also is a substance of the solid type at ambient temperature and liquefaction for dissolving occurs, in this case also, by heating it.

Diatomaceous earth is made from the fossilized remains of tiny, aquatic organisms called diatoms. Their skeletons are made of a natural substance called silica. The diatomaceous earth is added to the formulations to damage larvae and pupae after ingestion.

Peppermint oil is a colourless, pale yellow liquid with a strong agreeable smell and a powerful aromatic taste. Peppermint oil is the most popular and widely used essential oil employed in flavouring, pharmaceuticals, confectionery and medicines.

*Eucalyptus* essential oil is obtained from fresh leaves of the tall, evergreen *Eucalyptus* tree. The tree, scientifically classified as *Eucalyptus globulus* is also known as fever tree, blue gum tree or stringy bark tree, depending on where it is located in the world. The numerous health benefits of *eucalyptus* oil have attracted the attention of the entire world, and it has stimulated a great deal of exploration into its usage in aromatherapy as well as in conventional medicine.

According to the embodiments, one possible excipient is water.

From a practical point of view, some of the possible embodiments in application related to specific formulations of undisputed effectiveness and with negligible toxicity are cited hereafter in materials and methods.

The excipient amounts involved are to be considered purely to define the proportions among the various components.

It has thus been found that the invention achieves the intended aim and object.

The invention thus conceived is susceptible of numerous modifications and variations, all of which are within the scope of the appended claims.

All the details may further be replaced with other technically equivalent ones.

Moreover, it is noted that anything found to be already known during the patenting process is understood not to be claimed and to be the subject of a disclaimer.

In practice, the materials used, as well as the shapes and the dimensions, may be any according to requirements without thereby abandoning the scope of the protection of the appended claims.

MATERIALS/METHODS

Components

Components: tyrosine, cetyl alcohol, salicylic acid, peppermint oil, *eucalyptus* oil, diatomaceous earth and tween 20.

Several formulations were tested to evaluate their larvicidal/pupicidal activity:
 i) 0.03 g of tyrosine dissolved in 200 ml breeding water;
 ii) 10 g of cetyl alcohol and 10 g of salicylic acid dissolved into 100 ml of peppermint oil (solution A).
 iii) 10 g of cetyl alcohol, 10 g salicylic acid, 5 g diatomaceous earth and 20 drops of tween 20 dissolved into 40 ml of *eucalyptus* oil and 60 ml of peppermint oil (solution B);

The solutions A and B were shaken vigorously before use to obtain an excellent emulsion.
 iv) 0.03 g of tyrosine dissolved directly into the breeding water (200 ml) containing larvae, pupae in addition to 5 drops of solution A;
 v) 0.03 g of tyrosine dissolved directly into the breeding water (200 ml) containing larvae, pupae in addition to 5 drops of solution B;
 vi) a negative control containing only breeding water.

Larvae/Pupae Collection and Rearing

Larvae and pupae of *Anopheles gambiae, An. stephensi, Aedes albopictus* and *Ae. aegypti* were reared in 200 ml of breeding water and fed by mice dry-food powder in the mosquito insectary at the University of Camerino. The pre-adult developmental stages were grown under these conditions: 28° C., 80% relative humidity and a photoperiod of 12 h light followed by 12 h dark.

Larvicidal/Pupicidal Tests

Mosquito larvicidal/pupicidal tests were carried out based on the WHO standardized procedures and guidelines for larvicidal assay.

The screening was conducted evaluating the mortality of populations including first, second, third and fourth-instar larvae and pupae, using different experimental products:

- 0.03 g of tyrosine dissolved in 200 ml breeding water;
- 10 g of cetyl alcohol and 10 g of salicylic acid dissolved into 100 ml of peppermint oil (solution A).
- 10 g of cetyl alcohol, 10 g salicylic acid, 5 g diatomaceous earth and 20 drops of tween 20 dissolved into 40 ml of *eucalyptus* oil and 60 ml of peppermint oil (solution B);
- The solutions A and B were shaken vigorously before use to obtain an excellent emulsion.
- 0.03 g of tyrosine dissolved directly into the breeding water (200 ml) containing larvae, pupae in addition to 5 drops of solution A;
- 0.03 g of tyrosine dissolved directly into the breeding water (200 ml) containing larvae, pupae in addition to 5 drops of solution B;
- a negative control containing only breeding water.

For each mosquito species, 24 hours before the assay to reduce the larval stress, we prepared 6 trays [15 cm (width), 15 cm (length) and 6.5 cm (deep)] one for each tested products, containing 200 ml of breeding water which includes 40 mosquito larvae (first, second, third, fourth-instars) and 10 pupae. Each assay comprised of 3 replicates.

Mortality was recorded every 30 minutes from beginning for the pre-adult developmental stages (larvae and pupe). Larvae and pupae were considered dead when they failed to do any movement. The dead larvae and pupae were recorded, and the average percentage mortality was calculated.

RESULTS and DISCUSSION

The tyrosine alone caused a larval mortality of about 60% after 24 hours post application. The solution A and B showed to determine the death of 70% of larvae after 18 h post application whereas all the pupae die approximately in one hour. The larvicide composed by 0.03 g of tyrosine in addition to 5 drops of solution A and B in 200 ml of breeding water showed the stronger larvicidal/pupicidal activity determining the death of 100% mosquito larval stages after 2 hours post application and pupae after 15 min. A negative control including 40 larvae (from first to fourth-instars) and 10 pupe in 200 ml of breeding water alone, was also prepared for each species. No dead larvae or pupae were recorded from negative control samples.

The results show that all the compounds tested perform a synergistic and complementary action increasing the efficacy of each single ingredients tested alone.

CONCLUSIONS

The inventors have developed an innovative, low cost and safe larvicidal and pupicidal composition characterized by an insignificant toxicity for animals, particularly fishes, and for human beings.

The larvicide/pupicide formulation was developed as a tool against *Anopheles stephensi, An. gambiae, Aedes aegypti* and *Ae. albopictus* mosquito species, vectors of several diseases, such as malaria, dengue, Zika virus, chikungunya and yellow fever; through the use of few selected ingredients with a low toxicity able to kill larval and pupal stages.

One of the main advantage of the invention is its quick time of action on killing pre-adult stages of mosquito species listed above. Moreover, the larvicide formulation's most important feature is related to the nature of its compounds: since tyrosine is essential for mosquito physiology it doesn't undergo through resistant mechanisms developed by mosquitoes against the synthetic compounds present in common larvicides and insecticides.

Results suggest that our safe larvicide/pupicide can represent a powerful competitor against the common used chemical products which toxicity and collateral effects on human and animals are not well characterized.

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

REFERENCES

Rodolfo Quevedo and Nelson Nuñez-Dallos Martha L. Quinones. (2015). Larvicidal activity of single and macrocyclic tyrosine derivatives against three important vector mosquitoes. Research on Chemical Intermediates. 41 (8): 5283-5292.

The invention claimed is:

1. An emulsion for killing mosquito larvae, comprising:
   a) tyrosine dissolved in water; and
   b) a solution of cetyl alcohol and salicylic acid dissolved in peppermint oil,
   wherein the emulsion is configured to be applied as a larvicide to kill larvae of mosquitoes selected from a group consisting of *Anopheles gambiae, Anopheles Stephensi, Aedes aegypti* and *Aedes Albopictus*.

2. The emulsion of claim 1, wherein the solution further comprises diatomaceous earth, tween 20 and *eucalyptus* oil dissolved in said peppermint oil.

3. The emulsion of claim 1, wherein the emulsion kills the larvae within about two hours and fifteen minutes, respectively.

4. The emulsion of claim 1, wherein the emulsion comprises 0.03 g of said tyrosine, 200 ml of said water, 10 g of said cetyl alcohol, 10 g of said salicylic acid and 100 ml of peppermint oil.

5. The emulsion of claim 2, wherein the emulsion comprises 0.03 g of said tyrosine, 200 ml of said water, 10 g of said cetyl alcohol, 10 g of said salicylic acid, 5 g of diatomaceous earth and 20 drops of tween 20 dissolved into 40 ml of *eucalyptus* oil and 60 ml of peppermint oil.

6. The emulsion of claim 1, wherein the ratio of tyrosine to water in the emulsion ranges from 0% to 1%.

7. The emulsion of claim 1, wherein the ratio of cetyl alcohol to peppermint oil ranges from 0% to 30%.

8. The emulsion of claim 1, wherein the ratio of salicylic acid to peppermint oil ranges from 0% to 30%.

9. The emulsion of claim 2, wherein the ratio of diatomaceous earth to peppermint oil ranges from 0% to 20%.

10. The emulsion of claim 2, wherein the ratio of tween 20 to peppermint oil ranges from 0% to 20%.

11. The emulsion of claim 2, wherein the ratio of *eucalyptus* oil to peppermint oil ranges from 0% to 70%.

12. The emulsion of claim 1, wherein the larvae mortality is at least 60% after 24 hours post application of said emulsion.

13. The emulsion of claim 1, wherein the larvae mortality is at least 70% after 18 hours post application of said emulsion.

14. The emulsion of claim 2, wherein the larvae mortality is approximately 100% after 2 hours and 15 minutes post application of said emulsion, respectively.

15. An emulsion for killing mosquito larvae, comprising:
   c) tyrosine dissolved in water; and
   d) an oil-based solution comprising peppermint oil,
   wherein the emulsion is configured to be applied as a larvicide to kill larvae of mosquitoes selected from a group consisting of *Anopheles gambiae, Anopheles Stephensi, Aedes aegypti* and *Aedes Albopictus*.

16. The emulsion of claim 15, wherein the oil-based solution comprises cetyl alcohol.

17. The emulsion of claim 15, wherein the oil-based solution comprises salicylic acid.

18. A method for killing mosquito larvae, wherein the method includes administering the larvicide emulsion of claim 1 as a larvicide to kill larvae of mosquitoes.

\* \* \* \* \*